(12) United States Patent
Li

(10) Patent No.: US 7,968,054 B1
(45) Date of Patent: Jun. 28, 2011

(54) NANOSTRUCTURE SENSING AND TRANSMISSION OF GAS DATA

(75) Inventor: Jing Li, San Jose, CA (US)

(73) Assignee: The United States of America as represented by the Administrator of the National Aeronautics and Space Administration (NASA), Washington, DC (US)

( * ) Notice: Subject to any disclaimer, the term of this patent is extended or adjusted under 35 U.S.C. 154(b) by 941 days.

(21) Appl. No.: 11/715,785

(22) Filed: Mar. 7, 2007

(51) Int. Cl.
G01N 7/00 (2006.01)
G01N 33/48 (2006.01)
G01N 27/00 (2006.01)
G01N 31/00 (2006.01)
G01N 19/00 (2006.01)

(52) U.S. Cl. ............. 422/83; 422/68.1; 422/98; 702/22; 702/23; 702/27; 702/30; 977/953; 977/957; 977/742; 977/842

(58) Field of Classification Search ............... 702/27; 700/266
See application file for complete search history.

(56) References Cited

U.S. PATENT DOCUMENTS

| | | | | |
|---|---|---|---|---|
| 6,289,328 | B2 * | 9/2001 | Shaffer | 706/20 |
| 6,433,702 | B1 | 8/2002 | Favreau | |
| 7,312,095 | B1 * | 12/2007 | Gabriel et al. | 438/49 |
| 7,318,908 | B1 * | 1/2008 | Dai | 422/68.1 |
| 7,477,993 | B2 * | 1/2009 | Sunshine et al. | 702/22 |
| 7,623,972 | B1 * | 11/2009 | Li et al. | 702/27 |
| 2003/0175161 | A1 * | 9/2003 | Gabriel et al. | 422/90 |
| 2005/0233325 | A1 * | 10/2005 | Kureshy et al. | 435/6 |
| 2007/0202012 | A1 * | 8/2007 | Steichen et al. | 422/98 |

OTHER PUBLICATIONS

Janata, Electrochemical Sensors, Principles of Chemical Sensors, 1989, 81-239, Plenum Press, New York.
Kong, et al., Nanotube Molecular Wires as Chemical Sensors, Science, Jan. 28, 2000, 622-625, 287, AAAS.
Li, Chemical and Physical Sensors, Carbon Nanotubes: Science and Applications, 2004, 213-233, Editor: M. Meyyappan, CRC Press, Boca Raton, FL.
Li, et al., Carbon Nanotube Sensors for Gas and Organic Vapor Detection, NanoLetters, 2003, 929-933, 3-7, American Chemical Society.
Liao, et al., Telemetric Electrochemical Sensor, Biosensors Bioelectronics, 2004, 482-490, 20, Elsevier B.V.
DWL-AB650, a commercial product, D-Link Systems Inc., http://www.dlinkshop.com/.
MICAz, a commercial product, Crossbow Technology Inc., http://www.xbow.com/.
Nanotechnology Innovation for Chemical, Biological, Radiological, and Explosive (CBRE) Detection and Protection, Workshop Report, Nanoscale . . . , Nov. 2002, http://www.nano.gov.

* cited by examiner

*Primary Examiner* — In Suk Bullock
*Assistant Examiner* — Jennifer Wecker
(74) *Attorney, Agent, or Firm* — John F. Schipper; Robert M. Padilla

(57) ABSTRACT

A system for receiving, analyzing and communicating results of sensing chemical and/or physical parameter values, using wireless transmission of the data. Presence or absence of one or more of a group of selected chemicals in a gas or vapor is determined, using suitably functionalized carbon nanostructures that are exposed to the gas. One or more physical parameter values, such as temperature, vapor pressure, relative humidity and distance from a reference location, are also sensed for the gas, using nanostructures and/or microstructures. All parameter values are transmitted wirelessly to a data processing site or to a control site, using an interleaving pattern for data received from different sensor groups, using I.E.E.E. 802.11 or 802.15 protocol, for example. Methods for estimating chemical concentration are discussed.

10 Claims, 13 Drawing Sheets

NANOSTRUCTURE SENSING AND TRANSMISSION OF GAS DATA

ORIGIN OF THE INVENTION

Work related to this invention was performed under a joint research agreement between the National Aeronautics and Space administration and the University of California.

FIELD OF THE INVENTION

This invention relates to wireless transmission of data provided by nanostructure-based chemical and physical sensors.

BACKGROUND OF THE INVENTION

Chemical sensors have been developed for decades to detect various concentration levels of gases and vapors for deployment in a wide range of applications in industry, space mission, environment monitoring, medical, military, and others. The detection usually centers on change in a particular property or status of the sensing material (such as thermal, electrical, optical, mechanical, etc) upon exposure to the species of interest. The sensing material may be any of several elements from the periodic table, plus inorganic, semiconducting and organic compounds, in bulk or thin film form. One of the most investigated classes of chemical sensors in the past is the high-temperature metal oxide sensors due to these sensors' high sensitivity at low ppm to ppb concentration levels, with tin oxide thin films as an example. Polymer sensors have been studied in recent years because they can be operated at room temperature with low power consumption and are easily fabricated. Although commercial sensors based on these materials are available, continued research is in progress with sensing technologies using new sensing materials and new transducer platforms. New sensing technologies, such as nanotechnology-based sensors, are being developed to overcome the large power consumption and poor selectivity of metal oxides sensors, and to improve the poor sensitivity and narrow detection spectrum of polymer sensors.

Typical figures of merit expected from a chemical sensor include sensitivity (even down to a few molecules, selectivity, low power consumption, rapid response time and rapid sensor recovery time. Sensors based on the emerging nanotechnology may provide improved performance on all of the above aspects compared to current micro and macro sensors. Nanomaterials exhibit small size, light weight, very high surface-to-volume ratio, and increased chemical reactivity compared to bulk materials; all these properties are ideal for developing extremely sensitive detectors. The potential of nanomaterials for detection and for protection and remediation has been outlined in a recent report by the National Science and Technology Council ("Nanotechnology Innovation for Chemical, Biological, Radiological and Explosive Detection and Protection," November 2002).

One promising nanomaterial is the carbon nanotube ("CNT"), which exhibits extraordinary mechanical, electrical and optical properties. These interesting properties have prompted wide range investigations for applications in nano-electronics, high strength composites, field emitting devices, catalysts, etc. A single-walled carbon nanotube ("SWCNT") has all the atoms on the surface and therefore would be exposed maximally to the environment, allowing a change in its properties sensitively. The first demonstration of an SWCNT-based sensor was for a chemical field effect transistor ("CHEMFET"), where a single semiconducting SWCNT is used as the channel material and the conductivity was shown to change upon exposure to $NO_2$ and $NH_3$ (J. Kong et al, "Nanotube Molecular Wires as Chemical Sensors," Science, vol. 287, pp 622-625, January 2000). The potential for using CNTs in chemical sensors was noted in the Kong et al article. However, it still is a challenge to make practical sensors, due to difficulty in fabrication complexity, low sensor yield and poor reproducibility.

A different configuration of carbon nanotube-based chemical sensors with much easier fabrication process was introduced by J. Li et al in "Chemical and Physical Sensors, Carbon Nanotubes: Science and Applications", M. Meyyappan, ed., CRC Press, Boca Raton, Fla., 2004. First, an interdigitated electrode ("IDE") configuration is fabricated using conventional photolithographic methods with a nominal finger width of 10 μm and gap size of 8 μm. The electrode fingers are made of thermally evaporated Ti and Au (20 nm and 40 nm thickness, respectively) on a layer of $SiO_2$, thermally grown on top of a silicon wafer. Second, a thin layer of carbon nanotubes forming a network is laid on the fingers using a solution casting process. The conductivity of the CNT network changes upon exposure of the fingers to different gases or vapors. Such a process is significantly simpler and produces consistent sensors based on statistical properties of the CNT network with high yield (~100 percent). The IDE configuration facilitates effective electric contact between SWCNTs and the electrodes over large areas, while providing good accessibility for analytes in the form of gas/vapor adsorption or contaminants adsorption/extraction in/from liquid to all SWCNTs including semiconducting tubes.

Although carbon nanotube-based chemical sensors using the IDE configuration have been prototyped in laboratories, use of an IDE configuration for wireless sensing has not been reported in published research. Use of an IDE configuration requires frequent transmission of data measured at each of a large number of IDE fingers. A straightforward approach may consume substantial power and may require use of a relatively large footprint for the sensor system. This may be inconsistent with automated use of a remote system in a confined space.

What is needed is a wireless transmission system that (1) has a small footprint and whose size is compatible with a nanosensor system, which may have a diameter as small as 5-15 cm, (2) consumes relatively little power (e.g., about 50 μWatt-60 mWatt, or smaller with voltage regulation not activated), (3) is reliable, with a mean time to failure exceeding 8 hours (representative battery life) and (4) permits frequent data transmission from each of a large number of data sources.

SUMMARY OF THE INVENTION

These needs are met by the invention, which provides a system with one or more sensors for selected chemicals (all using nanostructure sensors with small physical sizes), one or more sensors for physical parameters, a multiplexer to receive and interleave the measured data stream values from the sensors according to a selected interleaving pattern, and a wireless transmission module to transmit the measured values to a receiver and data analyzer.

The overall sensor system consists of a chemical sensor module, a microcontroller-based data acquisition module, a multiplexer and constant current source module, and a wireless communication module. The chemical sensor module is based on use of an interdigitated electrode ("IDE") configuration. A layer of single-walled carbon nanotubes ("SWCNTs") is laid on the IDE fingers. Chemical sensing is based on detection of changes in the conductivity of the SWCNT network. In one embodiment, the system has 32 channels of chemical sensing elements. It is self-contained and portable, and wirelessly transmits measurement data to a PC, using an I.E.E.E. 802.11a, 802.11b or 802.15 wireless LAN protocol. The footprint of the invention has a diameter as small as a few cm.

DESCRIPTION OF BEST MODE OF THE INVENTION

Figure 1:
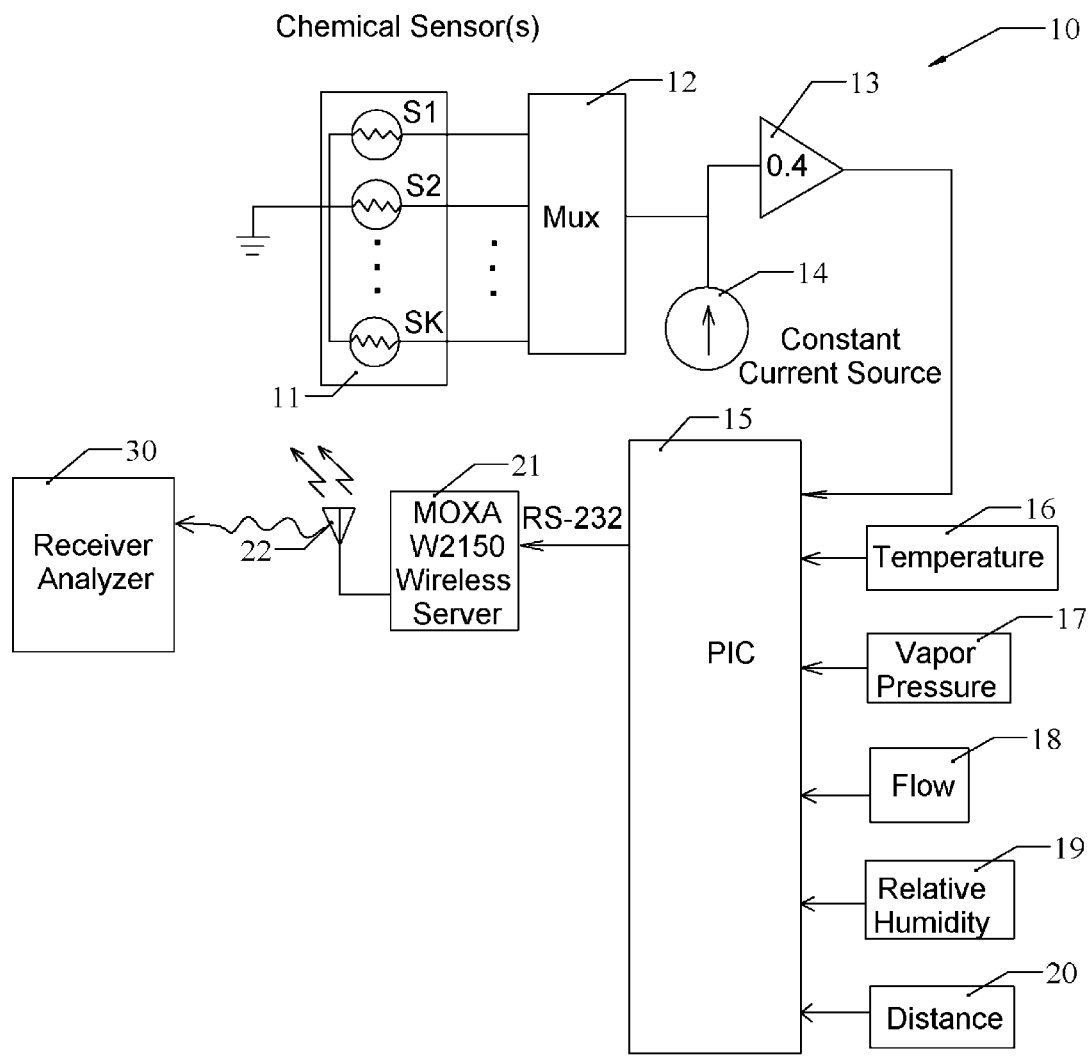
FIG. 1 schematically illustrates a sensor array and a wireless transmitter according to an embodiment of the invention.

FIG. 1 schematically illustrates components of a system 10, constructed according to the invention, including a chemical and/or physical nanosensor module 11, whose output signals are received by a multiplexer ("MUX") 12. An output signal of the MUX 12 is augmented by a constant current source 13 and is passed through a buffer amplifier 14 (optional) and is received and processed by a microcontroller 15 (e.g., a PIC16F688, available from Microchip Technologies). In one embodiment, wherein an array of carbon nanostructures is applied to environmental sensing, the microcontroller 15 also receives a signal from at least one of a temperature microsensor 16, a vapor pressure microsensor 17, a flow microsensor (direction, velocity) 18, a relative humidity microsensor 19 and an acoustic or electromagnetic distance sensor 20. The microcontroller output signals (e.g., in RS-232 format) are received by a wireless communication module 21, which includes a wireless server 22 (e.g., a MOXA W2150), which transmits these signals, using 802.11b protocol, through an antenna 23 to a local area network (LAN). The transmitted signals are received by a receiver (not shown) that is spaced apart from the transmission system 11, for display and/or further signal processing.

Each of the individual sensors, such as 16, 17, 18 and 19, has its own data reporting cycle, and it is assumed herein that these reporting cycles are numerically compatible. In a first approach, each of the reporting cycles has the same length $\Delta t$, and the four sensors report to a multiplexer in a consecutive interleave pattern as $t_{m,n} = \{16, 17, 18, 19, 16, 17, 18, 19, 16, 17, \ldots\}$ (n=1, 2, 3, 4; m=1, 2, ...) In a second version, at least one of the sensors (16) has a reporting cycle length that is N times as long as the other cycle lengths (e.g., N=3), and the four sensors report in a second interleave pattern as $t_{m,n} = \{16, 17, 18, 19, 17, 18, 19, 16, 17, 18, 19, 17, 18, \ldots\}$. In a third version, the reporting cycle lengths are rational, non-integer, multiples of each other so that the reporting pattern appears random, for example, where $\Delta t(16) = (7/4)\Delta t(17) = (3/5)\Delta t(18) = (7/4)\Delta t(19)$, a consistent third interleave pattern is: $t_{m,n} = \{16, 18, 16, 17, 18, 18, 19, 16, 18, 18, 16, 17, 18, 19, \ldots\}$. For any interleave pattern $\{t_{m,n}\}_{m,n}$ for data reporting, the multiplexer transmits the received data in another time sequence $\{t'_{m,n}\}_{m,n}$, where $t'_{m,n}$ is determined with reference to $t_{m,n}$ (e.g., $t'_{m,n} = t_{m,n} + \Delta t$, where $\Delta t$ is a substantially constant time delay value).

In one embodiment, the chemical sensor module contains 32 sensing elements, arranged in an IDE configuration, having pure SWCNTs, having polymer coated SWCNTs, and/or having metal nanoclusters or doped SWCNTs. At the center of the data acquisition system is a microcontroller (PIC16F688) from Microchip Technologies Inc. that samples each sensor element through a set of four Texas Instruments CD4051 multiplexers. Each MUX 12 reads signals from a group of eight chemical sensing elements. The LM234 constant current source from National Semiconductor is used to provide a constant current (100 μAmp) to each sensing element. Four of these devices are used to excite each group of eight chemical sensing elements. Conductivity or resistance is measured by supplying a constant current and measuring the corresponding voltage difference across the sensor. Also included in the data system is an AD22100K temperature sensor from Analog Devices. The microcontroller reads all 32 chemical sensor and temperature values and generates a serial data output that can be connected directly (1) to a wireless serial device server, for wireless data transmission, or (2) to an RS-232 serial data output for a PC, for data logging. In this design, a W2150 serial server from Moxa Technologies, Inc. is used to wirelessly transmit data to a laptop or to a desktop PC, using an I.E.E.E. 802.11b wireless LAN protocol.

An alternative server is a Crossbow MICAz, using an I.E.E.E. 802.15.4 protocol at 2.4 GHz, can also be used for wireless transmission. This system has a data transport rate of 250 kbits/sec, and each node can also serve as a router. This allows a subset of one or more nodes to serve as a collection point for collecting data that were measured elsewhere and routing the data to a data processing module and/or to a control site that can respond to any problem encountered in the data measurements or data processing. This system uses direct sequence spread spectrum radio transmission, which is useful where two or more data collection nodes are transmitting substantially simultaneously to a data processing module and/or to a control site. Transmission range is up to 100 M outdoors and up to 30 M indoors. Device dimensions are 58×32×7 mm (diameter ≈68 mm). Analog inputs as well as digital inputs are accepted by the MICAz system.

Another alternative server is an Air-Pro D-Link dual band wireless LAN, operating at 5 GHz and 2.4 GHz, using 801.11a/b protocol with 64/128 and 152-bit, shared key data encryption for authentication and enhanced data security. Each node can also provide data collection and forwarding to a data processing module and/or to a control site. Data transport rates are 1, 2, 5.5, 11 Mbits/sec (802.11b) and 6, 9, 12, 18, 24, 36, 48 and 54 Mbits/sec (802.11a). Transmission range is up to 400 M outdoors and up to 100 M indoors. Device dimensions are 118×54×13 mm (diameter ≈133 mm).

FIG. 1 schematically illustrates components of the system 10, which includes a chemical nanosensor module 11, whose sensor output signals are received by the MUX 12. The output signal from the MUX 12 is augmented by a constant current source 13, and this signal is passed through a buffer amplifier 14 (optional) and received by a microcontroller 15 (e.g., a PIC16F688, available from Microchip Technologies). The microcontroller 15 also receives a physical sensor signal from at least one of a temperature microsensor 16, a vapor pressure microsensor 17, a flow microsensor (direction, velocity) 18, a relative humidity microsensor 19 and an acoustic or electromagnetic distance sensor 20. The microcontroller output signals (presented, e.g., in RS-232 format) are received by a wireless server 21 (e.g., a MOXA W2150), which transmits these signals, using an I.E.E.E. 802.11b protocol, through an antenna 22 and are received by a receiver and analyzer 30, spaced apart from the transmission system 10, for display and/or further signal processing.

Sensor Response

Figure 2A:
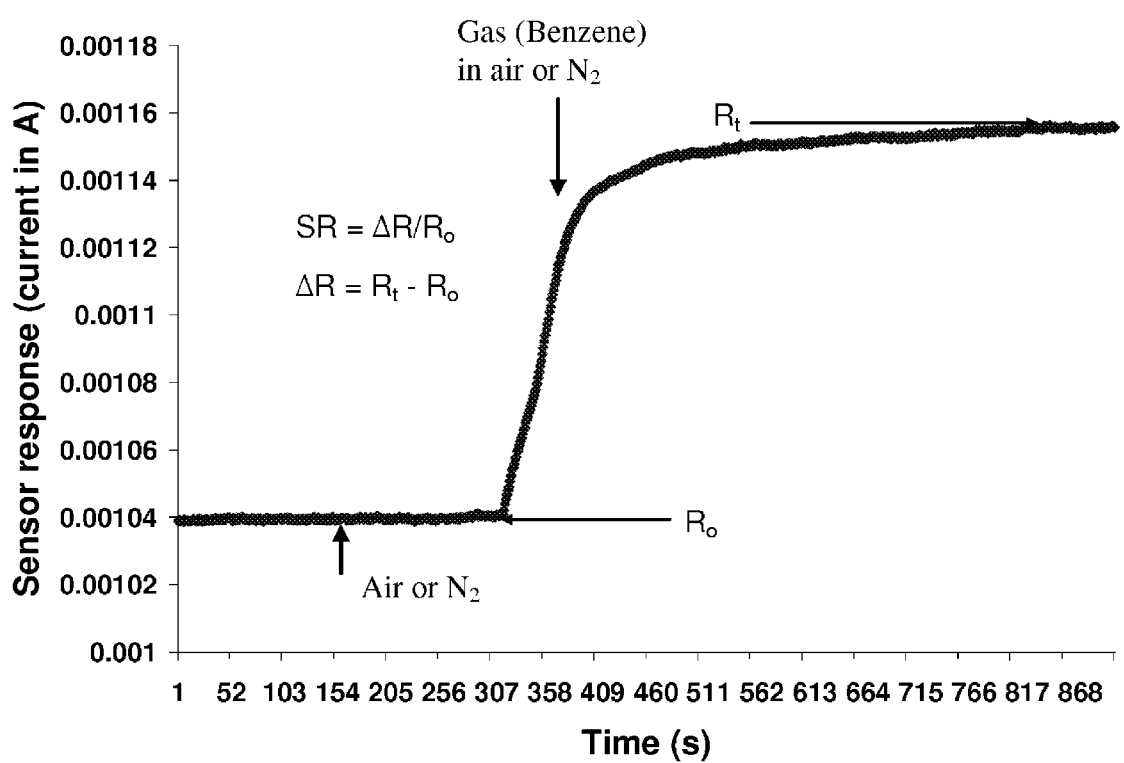
FIGS. 2A and 2B graphically illustrate sensor responses for identical exposures.
Figure 2B:
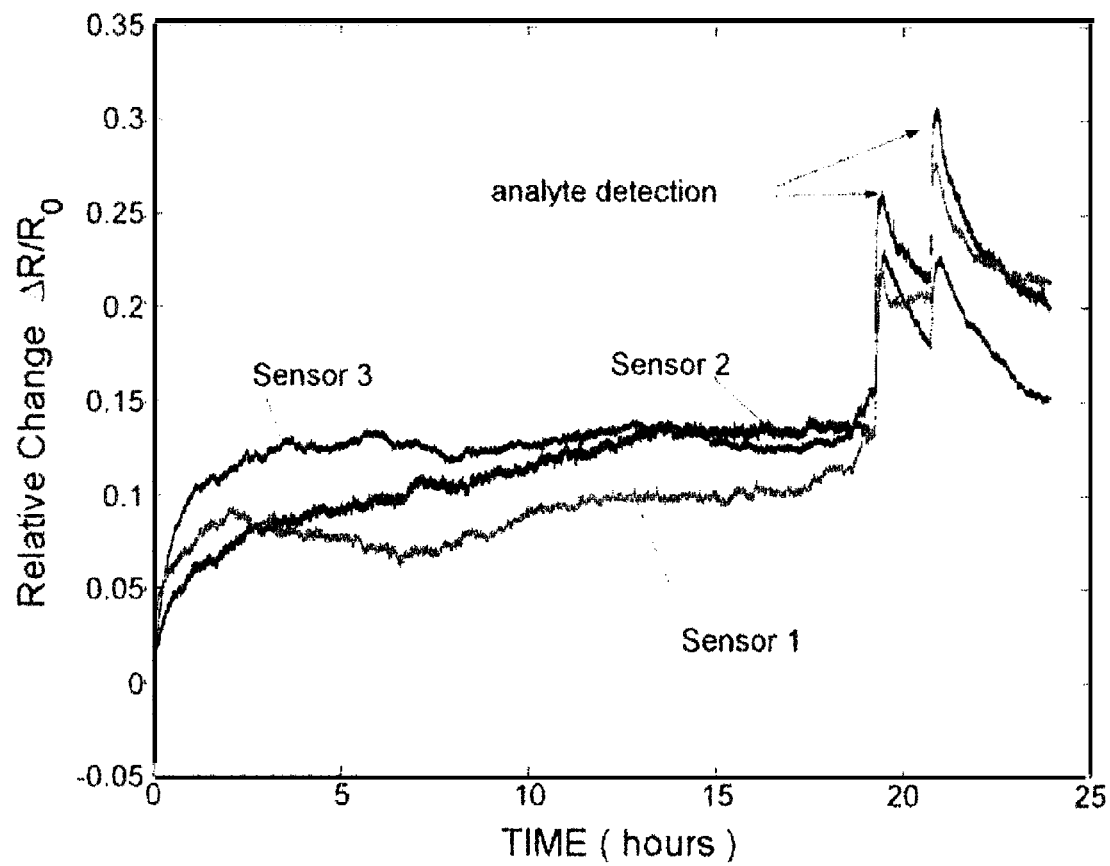

FIG. 2A shows typical sensor responses with the calculation. FIG. 2B shows the sensor responses from three identical sensors that were observed over a period of 25 hours from three sensing elements. The graph illustrates change of sensor resistance changes in response to the introduction of an analyte, in this case ammonia, at approximately t=19 hours and t=20.5 hours. Data from the sensors were collected at one sample per second. For this experiment, a cotton swab soaked in ammonia hydroxide solution was placed approximately 2 cm above the sensor surface, but the concentration of the analyte was not quantified. The sensor resistance for sensors x, y, and z increases approximately 10 percent from the sensor resistance measured just prior to the time(s) of detection of the analyte. Statistical properties of the measurement data were investigated to extract the information that presents the detection of analytes. Such information can be drawn from measurement data of a single sensor or from multiple sensors.

Figure 3:
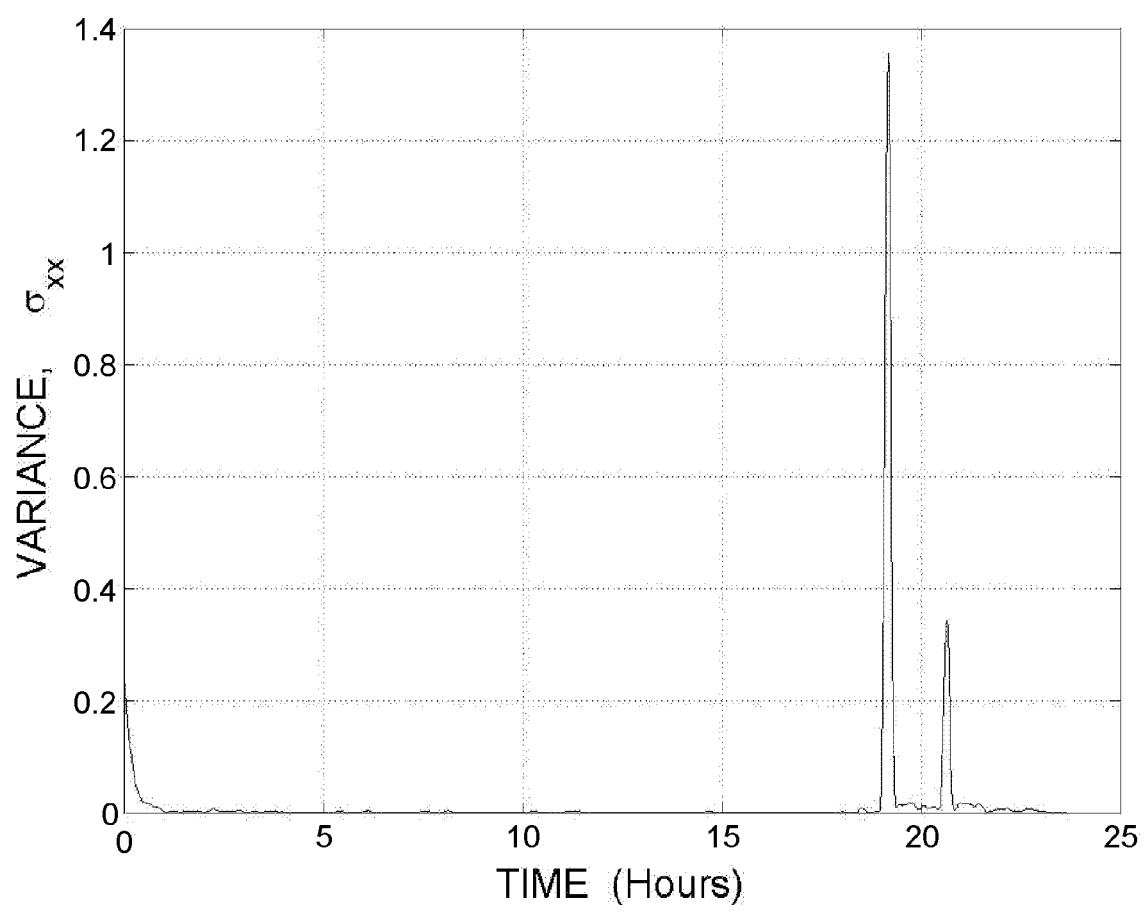
FIG. 3 shows the variance of measurement data from the sensor in FIGS. 2A and 2B, computed with a moving window of 1000 samples of the data.

FIG. 3 shows the variance of the measurement data from sensor "x" computed over a moving window of 1000 samples of the data. This window represents 16.7 minutes of measurement data. Small variance indicates small changes in measured data values over this period of time. A large variance indicates possible presence of analytes. In FIG. 3, this variance is substantially larger at two instants of time (t=19 and 20.5 hours) when the analyte is introduced.

Figure 4:
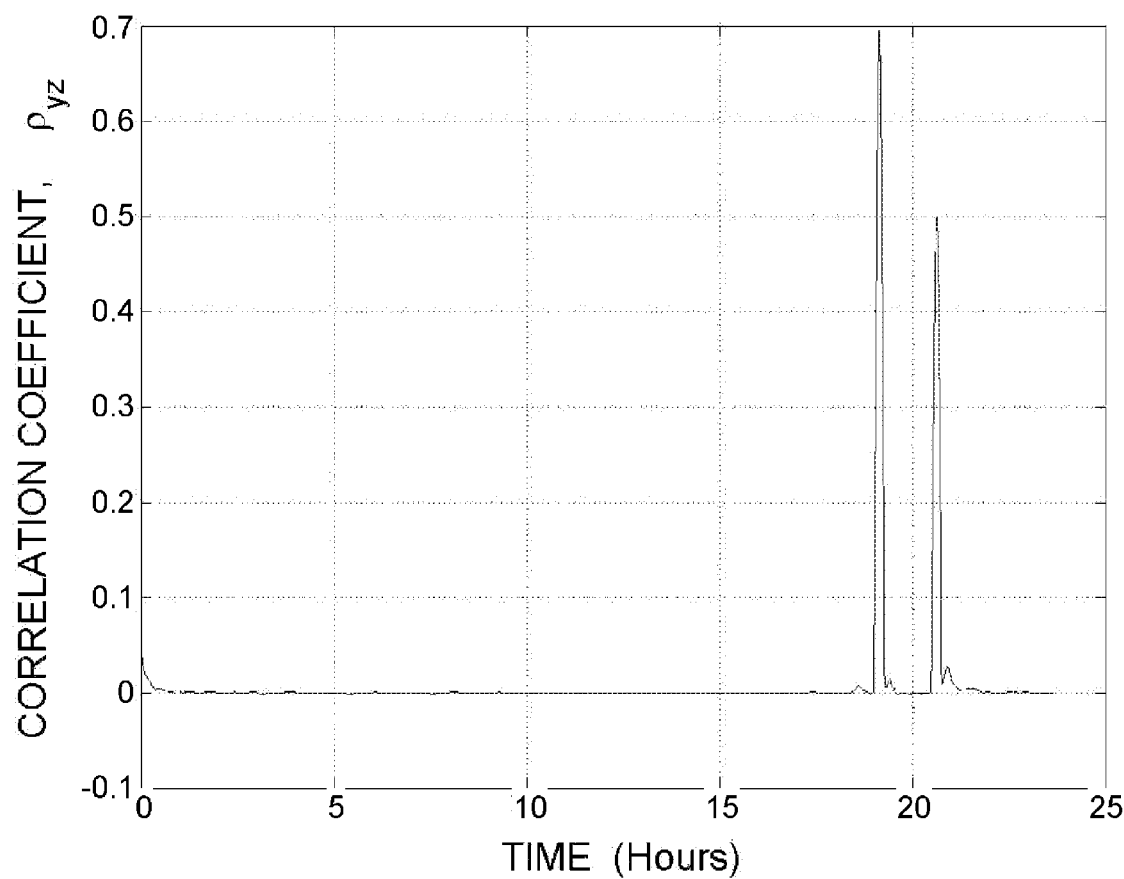
FIGS. 4 and 5 illustrate correlation of two sensors within a moving window.
Figure 5:
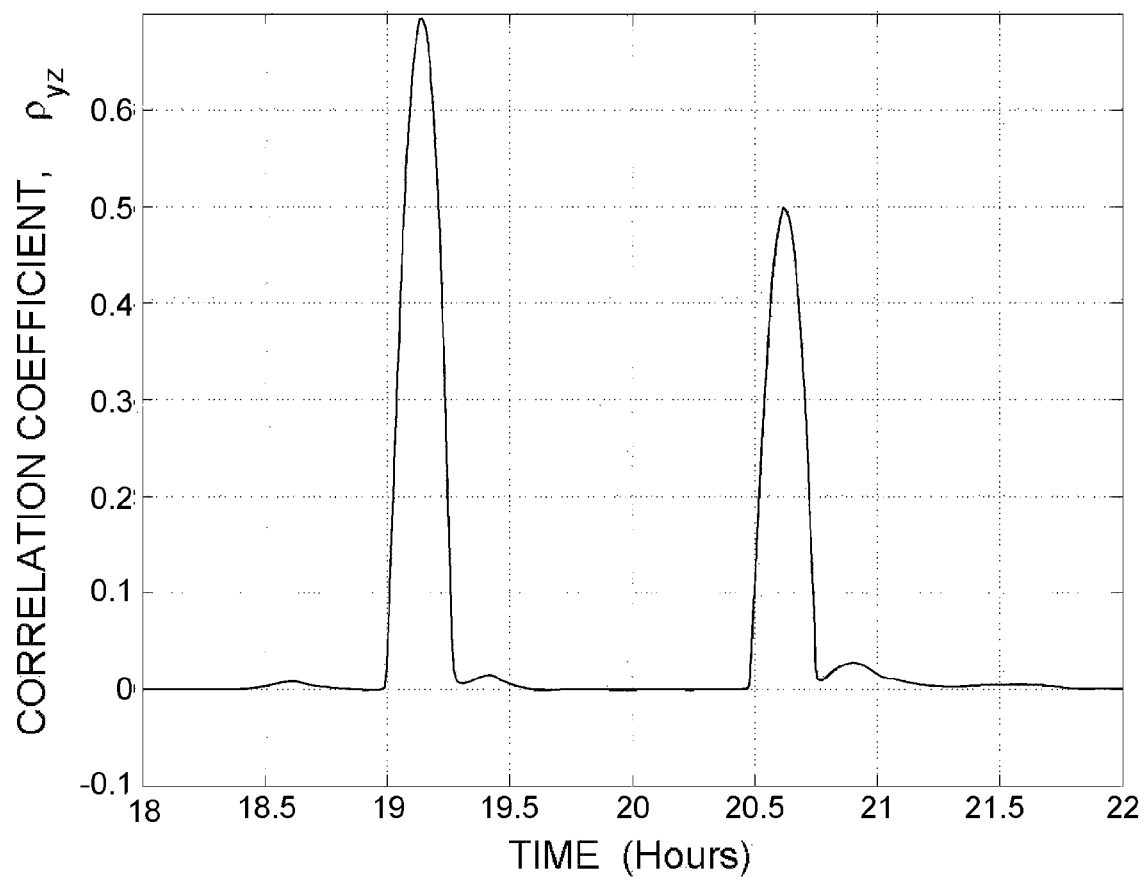
Figure 6:
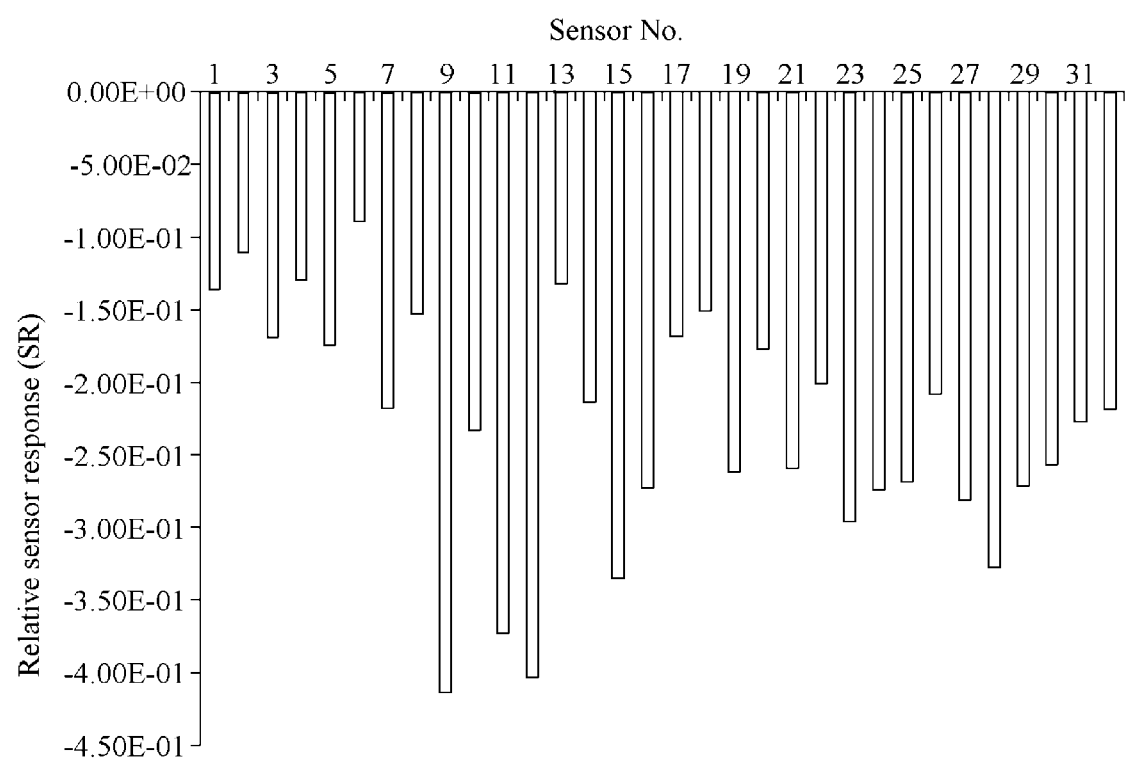
FIGS. 6 and 7 graphically illustrate relative chemical sensor response for exposure to $NO_2$ and for $Cl_2$, respectively.
Figure 7:
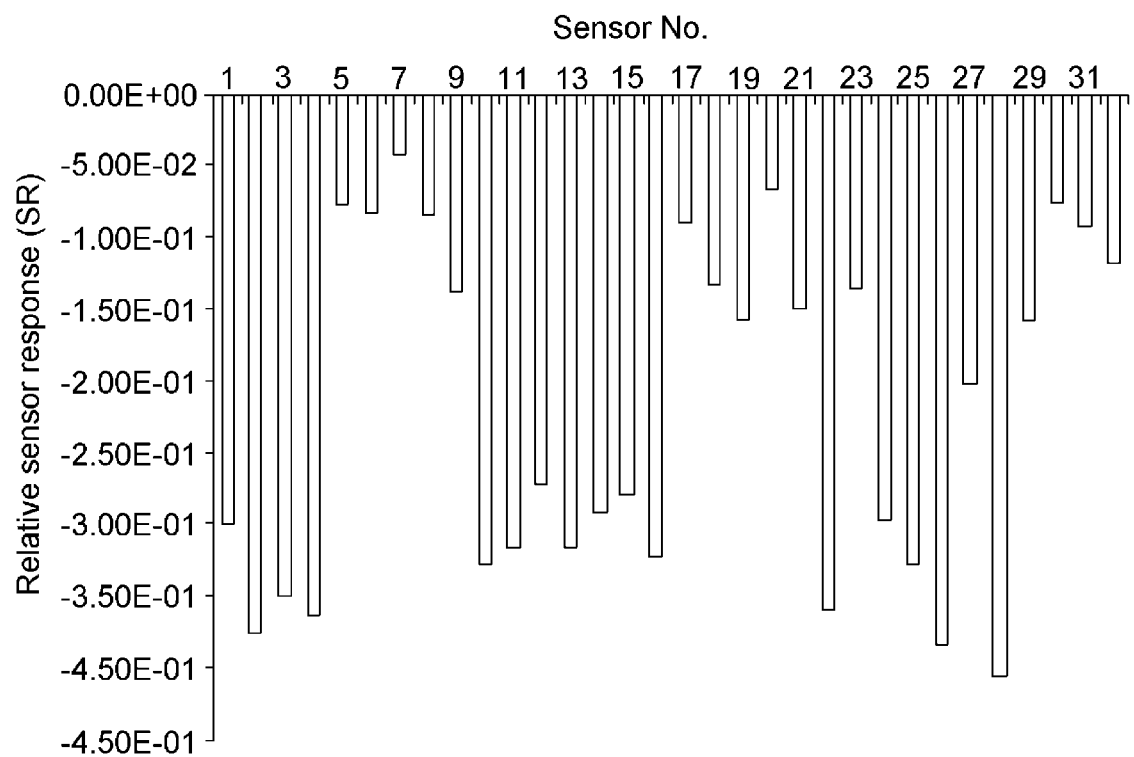

In addition to computing variance of individual sensor data values, statistical correlation of two sensors can be computed to confirm the presence of analytes. FIG. 4 shows the correlation coefficient for two sensors y and z, computed over the same moving window. FIG. 4 indicates, from an agreement between two sensors, that both sensors were exposed to the presence of analytes. An enlarged view of FIG. 4 around the two times of analyte introduction is shown in FIG. 5. Similar results were also observed for sensor pairs (x,y) and (x,z). FIGS. 6 and 7 graphically illustrate relative sensor response for exposure of the chemical sensor array to $NO_2$ gas and to $Cl_2$ gas, respectively. The functionalized sensor-to-sensor response differences can be used to determine or estimate the gas that is present.

Chemical Discrimination

The nanomaterials used in this array were individually studied for different gases and can be classified as: 1) pristine single walled carbon nanotubes, 2) carbon nanotubes coated with different polymers (here, chlorosulfonated polyethylene and hydroxypropyl cellulose), and 3) carbon nanotubes loaded with Pd nanoparticles and monolayer protected clusters of gold nanoparticles.

When exposed to a vapor-phase analyte, each sensing element in the array responds uniquely. A reproducible combination of resistances, or "smellprint", for each vapor/gas is manifest. The sensor response is measured as a bulk relative resistance change (alternatively, current change or voltage change): $\Delta R/R_0$, as in FIG. 3A. To calculate the relative sensor response (SR), the initial sensor resistance $R_0$ (or current/voltage), and the resistance R (or current/voltage) during the exposure are measured, and a normalized change, $$SR = \frac{R_t - R_o}{R_o} \quad (1)$$

is computed.

By comparing the results of several gases, it is possible to determine which sensors will respond in which manner (i.e. large or small amplitude, positive or negative). Looking at the histogram of sensor responses from 32 sensors to different gases/vapors, patterns for each gas/vapor can be established for discrimination between tested gases/vapors. When the sensor responses of an unknown subject gas are compared with the smellprints of several known substances, the unknown subject gas can be identified by matching its pattern to, or minimizing a pattern difference relative to, one of the known substances in the library.

However, the sensor responses often vary with concentration of the gas, temperature, and other external factors. To account for this, the data gathered by the sensors is normalized so that the relative responses can be compared, in order to make the sensor information more accurate. In normalization, the length of all data vectors becomes the same by making the sum of the squares of vector components equal to a constant so that the vectors become fixed length vectors. The data were normalized using:

$$\sum_{k=1}^{NV} x_{ik}^2 = c_i. \quad (2)$$

Here, k designates the sensor, i identifies the gas, and NV is the total number of sensors (32 in one embodiment). Theoretically, $c_i$ can be any positive number, such as 1.

In addition to analyzing the relative responses, the data are autoscaled to unit variance and zero mean, by mean-centering followed by dividing by the standard deviation:

$$x'_{ik} = \frac{x_{ik} - \bar{x}_k}{s_k} \quad (3)$$

where $x'_{ik}$ is the autoscaled response, $x_{ik}$ is the relative sensor response, $\bar{x}_k$ is the mean value of normalized response for that specific sensor, and $s_k$ is the standard deviation:

$$s_k = \left[ \frac{1}{NP-1} \sum_{i=1}^{NP} (x_{ik} - \bar{x}_k)^2 \right]^{1/2} \quad (4)$$

where NP is the number of independent responses. Autoscaling removes any inadvertent weighting that arises due to use of arbitrary physical units. In the absence of any information that would preclude its use, use of autoscaling is preferable for most applications.

Figure 8:
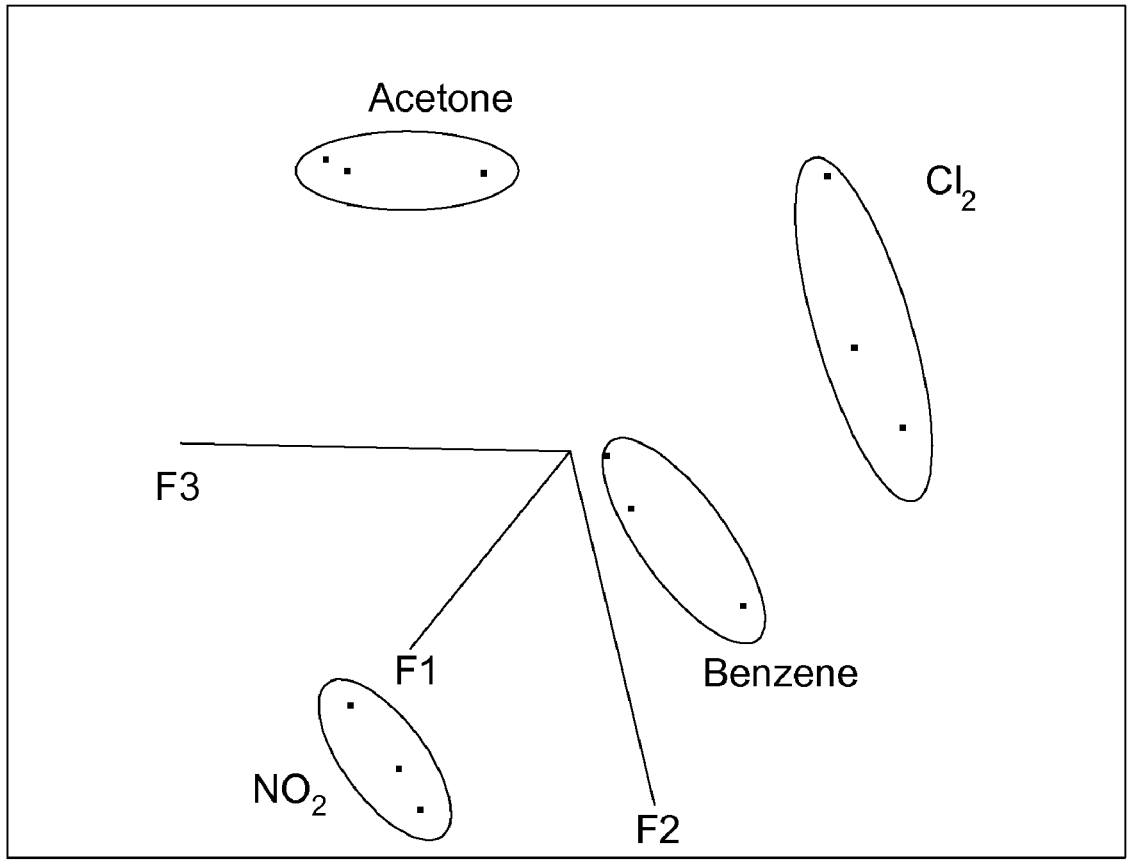
FIG. 8 graphically illustrates separation of the gases $NO_2$, $Cl_2$, benzene and acetone according to principal component analysis.
Figure 9:
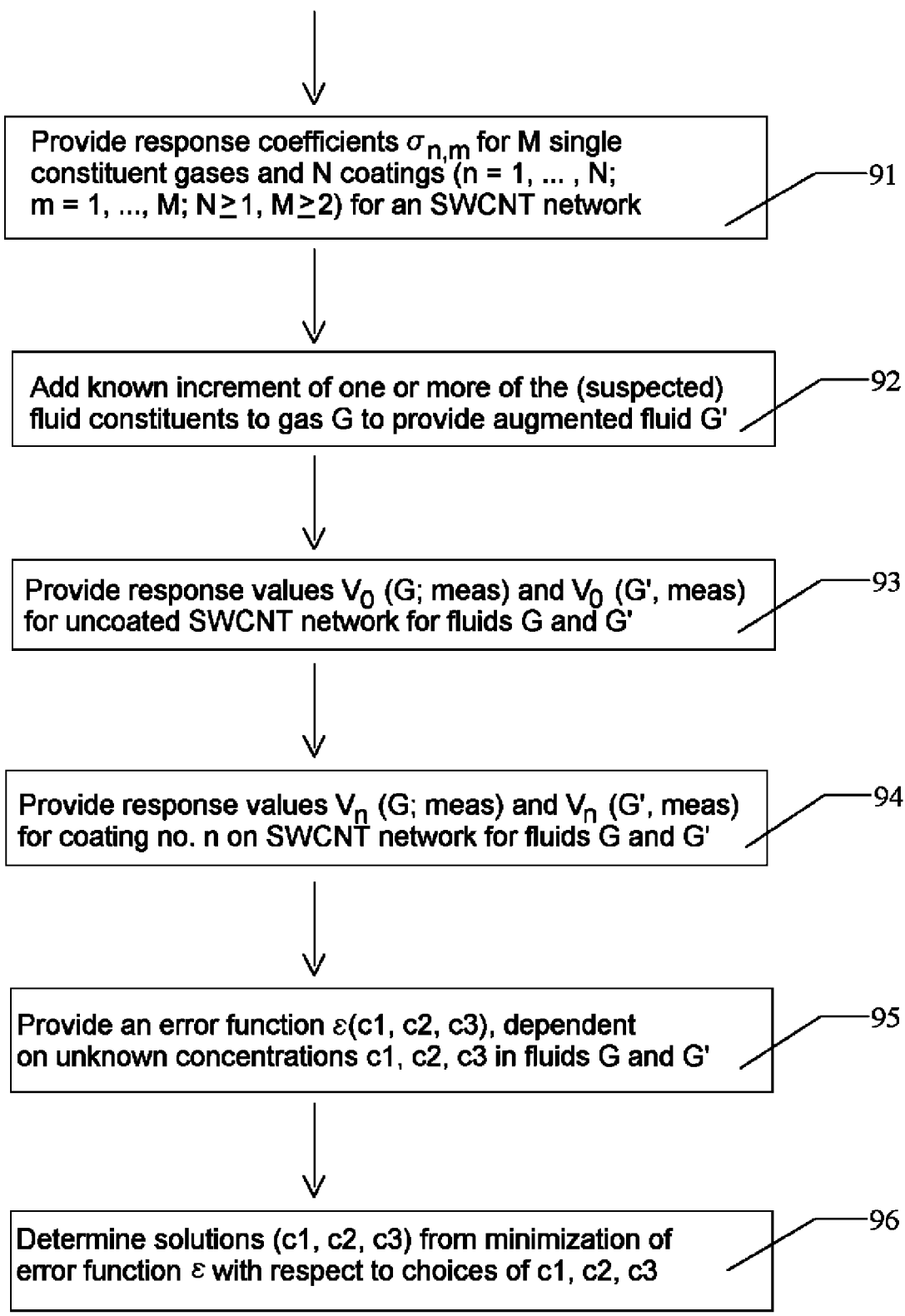
FIGS. 9, 10 and 11 are flow charts of algorithm procedures for estimating concentrations of initially unknown constituents according to the invention.
Figure 10:
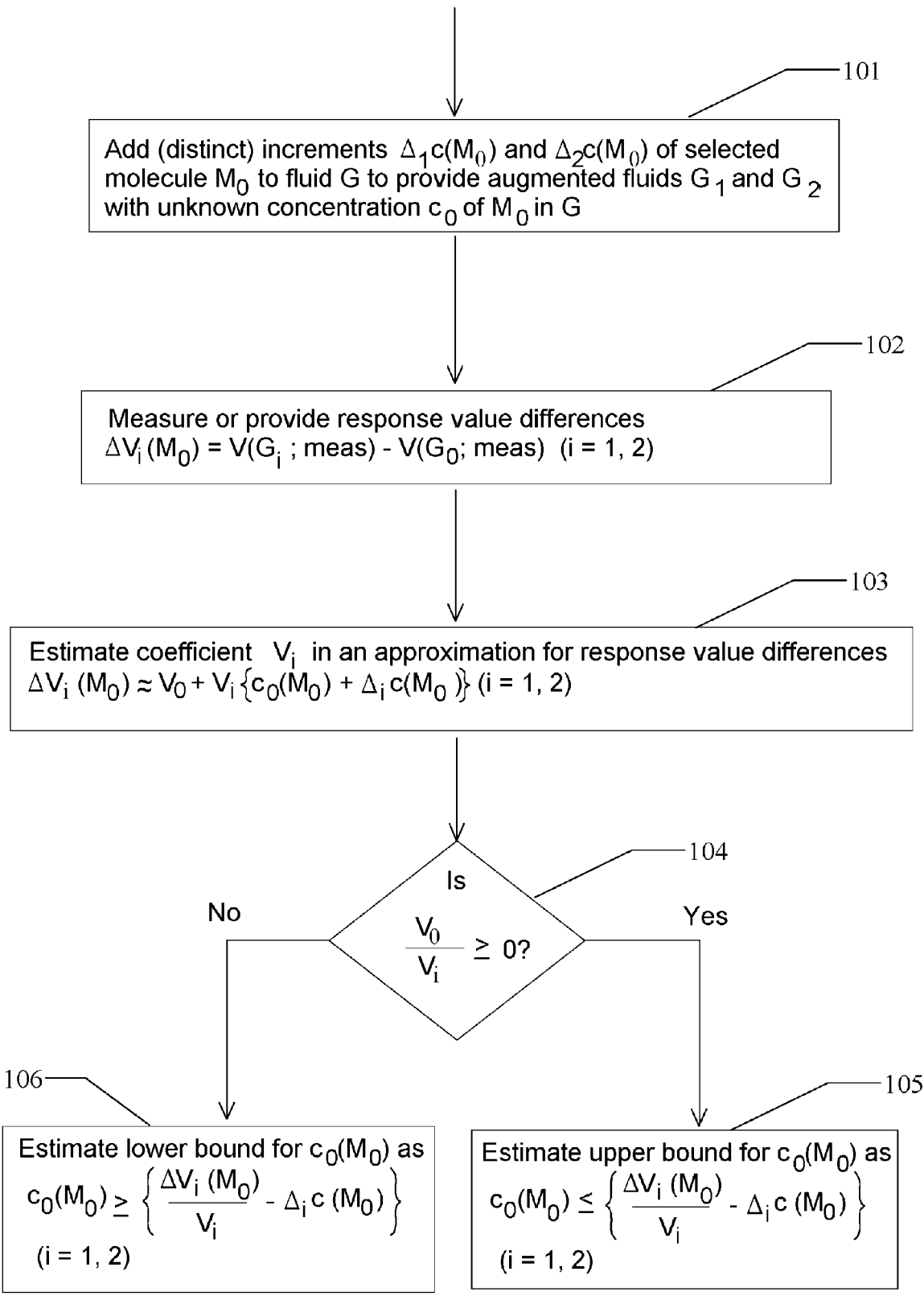
Figure 11:
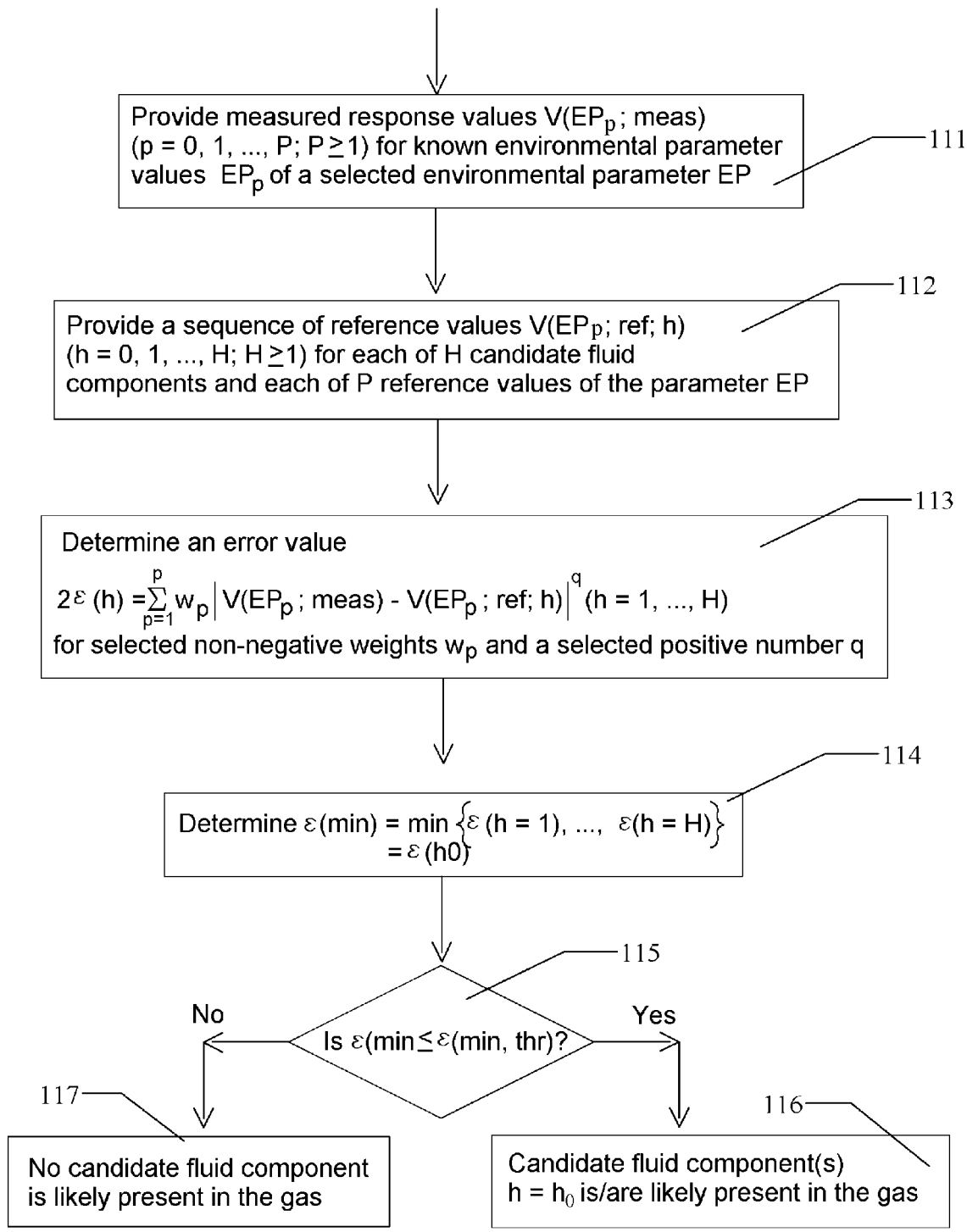

The processed data set contains the sensor responses from all 32 channels. Pattern recognition algorithms are very powerful tools to deal with a large set of data. For example, principal component analysis (PCA) was applied to the data set that was collected from this carbon nanotube based sensor array. The PCA is to express the main information in the variables $X = \{x_k | k=1, 2 \ldots K\}$ using a smaller number of variables $$\hat{T} = \{\hat{t}_1, \hat{t}_2 \ldots \hat{t}_A\} \ (A<K), \quad (5)$$

referred to as principal components of the variable X. In this instance, the X is a matrix of 32 sensor responses to these gases and vapors from the sensor array. Here, three principal components are labeled as F1, F2, and F3 that correspond to $\hat{t}_1, \hat{t}_2,$ and $\hat{t}_3$ in Eq. (5). FIG. 8 illustrates separation of the gases $NO_2$, $Cl_2$, benzene and acetone in terms of these three principal components.

These gases and vapors are completely separated in principal component space, which indicates that this sensor array provides a high discrimination power to these gases and vapors. Because these gases were tested by this sensor array at different concentration levels in the range of 5-45 ppm, this sensor array can be used (uniquely) for high sensitive gas and vapor detection and discrimination. This sensor array discriminates the gases and vapors by their chemical nature rather than their concentrations. Also, the array responses can discriminate between gases that have some similarity in their chemical nature.

Further analysis is often required to reliably estimate concentration of one or more target chemicals c0. After exposure of a nanostructure to a gas, a measured electrical parameter value EPV (e.g., impedance, conductivity, capacitance, inductance, etc.) changes with time in a predictable manner, if a selected chemical precursor is present, and will approach an asymptotic value promptly after exposure to the target chemical. The measured EPVs are compared with one or more sequences of reference EPVs for one or more known target precursor molecules, and a most probable concentration value is estimated for each of one, two or more target molecules. An error value is computed, based on differences for the measured and reference EPVs using the most probable concentration values. Where the error value is less than an error value threshold, the system concludes that the target molecule is likely. Presence of one, two or more target molecules in the gas can be sensed from a single set of measurements.

Figure 12:
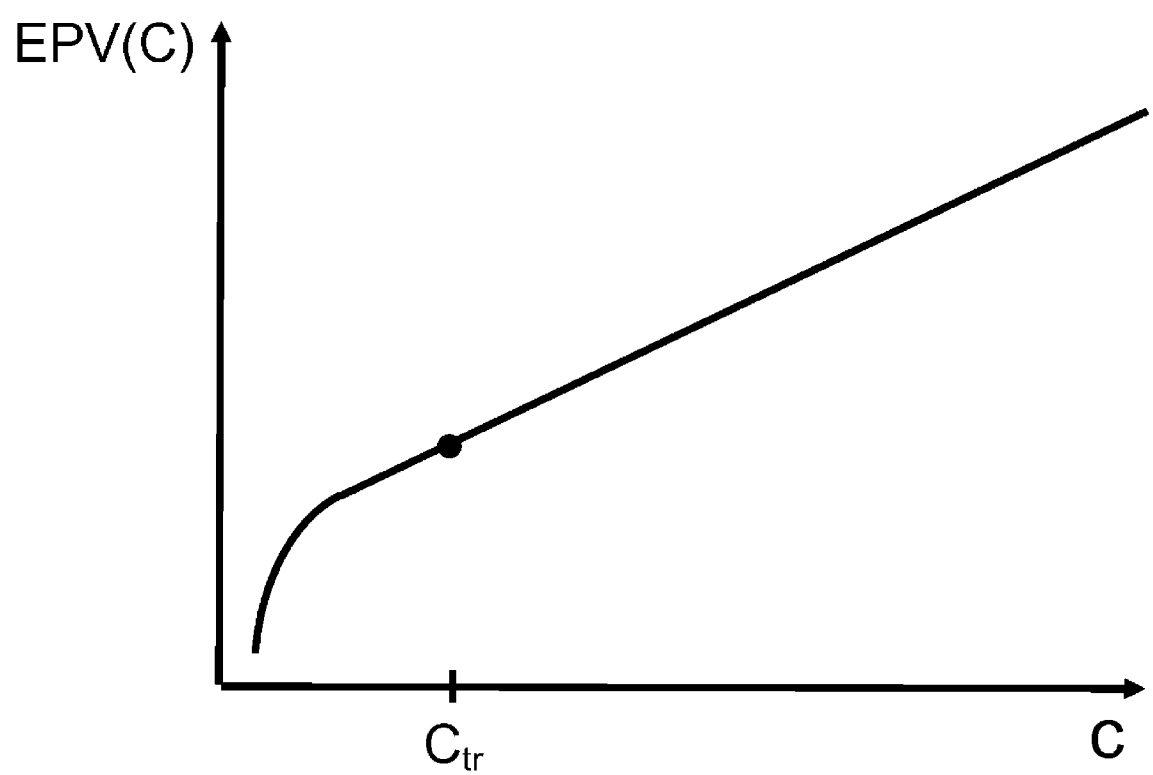
FIG. 12 graphically illustrates transition from linear to logarithmic dependence upon a variable, such as concentration.

For relatively large concentrations, it is assumed that the measured EPV for a given target molecule will vary linearly with the concentration C, $$EPV(C)=a+b\cdot C, tm \quad (6)$$

where the parameters a and b are characteristic of the particular target molecule for which the measurements are made. Where $EPV(C_{1,1})$ and $EPV(C_{1,2})$ are values for a pure substance measured at the different concentration values $C_{1,1}$ and $C_{1,2}$, respectively, the parameter values a and b can be estimated by $$a=\{EPV(C_{1,1})C_{1,2}-EPV(C_{1,2})C_{1,1}\}/\{C_{1,2}-C_{1,1}\}, \quad (7\text{-}1)$$

$$b=(EPV(C_{1,1})-EPV(C_{1,2}))/\{C_{1,2}-C_{1,1}\}, \quad (7\text{-}2)$$

for each target molecule. For smaller concentrations ($\approx$1-50 ppm), it may be preferable to use a logarithmic approximation, $$EPV(C)=a'+b'\cdot\log_e C, \quad (8)$$

where a' and b' are selected parameters. The parameter values a' and b' can be determined in a manner similar to that of Eqs. (7-1) and (13-2), by replacing the variables $C_{1,1}$ and $C_{1,2}$ by $\log_e\{C_{1,1}\}$ and $\log_e\{C_{1,2}\}$, respectively. FIG. 12 graphically illustrates the two concentration regimes for EPV(C), corresponding to Eqs. (6) and (8), which join together at a concentration transition value $C_{tr}$ for which $$a'+b'\cdot\log_e C_{tr}=a+b\cdot C_{tr}. \quad (9)$$

Given an array of N sub-arrays of CNS sensors and a set of K target molecules (k=1, . . . , K;K$\geq$2), the EPV data for the sensors can be pre-processed in order to identify more clearly which CNS sensor sub-arrays are more sensitive to presence of a particular target molecule. In a first embodiment, the array is exposed to a selected target molecule, such as $H_2O_2$, at a selected sequence $\{C_q\}_q$ (q=1, . . . , Q with Q=N) known (not necessarily distinct) concentration values (e.g., 500 ppm, 14,000 ppm, 65 ppm, 1200 ppm, 10 ppm, etc.), and a reference measurement value EPV(n;q;k;ref) (n=1, 2, . . . , N) is recorded for each sensor sub-array n, each concentration $C_q$ of a reference gas containing a selected target molecule (k). Measurements for one or more concentration values for the selected target molecule gas can be repeated, if desired, to obtain an N×N square matrix of values. With q fixed, an N×N matrix $\{EPV(n;q;k;ref)/EPV(n;k;norm)\}=E(n;q;k;ref)$ is formed, where, EPV(n;k;norm) is a normalization factor for the selected target molecule gas no. k and the sub-array no. n, which may be chosen as $$EPV(n;k;norm) = \left\{\sum_{q=1}^{N} u_q EPV(n;q;k;ref)^\rho\right\}^{1/\rho}, \quad (10)$$

where $\{u_q\}_q$ is a selected set of non-negative weight numbers whose sum is a selected positive number (e.g., 1 or N) and p is a selected positive number. The normalization factor E(n;k;norm) may be a single EPV (e.g., $u_{q1}=1$ and $u_q=0$ for q$\neq$q1), or may be a weighted sum of two or more EPVs. This normalization (optional) is intended to compensate for the concentration dependence of the particular target molecule.

For each sub-array n (fixed), the mean and standard deviation for each of K reference gases, numbered k=1, . . . , K (K$\geq$2) are computed, as $$\mu(n;k) = \sum_{q=1}^{N} E(n;q;k;ref)/N, \quad (11A)$$

$$\mu(n) = \sum_{k=1}^{K} \mu(n;k)/K, \quad (11B)$$

$$\sigma(n;k) = \left\{\sum_{q=1}^{N} \{E(n;q;k;ref)-\mu(n;k)\}^2/N\right\}^{1/2}, \quad (12A)$$

$$\sigma(n) = \sum_{q=1}^{N} \sigma(n;k)/K. \quad (12B)$$

One now forms K autoscaled N×N matrices, defined by $$S(n;q;k)=\{E(n;q;k;ref)-\mu(n)\}/\sigma(n), \quad (13\text{-}k)$$

and analyzes K eigenvalue equations $$S(n;q;k)\,V(k;\lambda(k))=\lambda(k)\,V(k;\lambda(k)), \quad (14\text{-}k)$$

where k (=1, . . . , K) is fixed and V(k;$\lambda$(k)) is a normalized N×1 vector that will usually depend upon the reference gas (k). If, as is likely, the N eigenvalues $\lambda$(k) for a fixed reference gas k are distinct, the corresponding eigenvectors V(k;$\lambda$,(k)) are mutually orthogonal (non-degeneracy). In the unusual event (degeneracy) that two or more of the N eigenvalues $\lambda$(k) are equal, different non-zero linear combinations of the corresponding eigenvectors V(k;$\lambda$(k)) can be constructed that are orthogonal to each other, within a sub-space spanned by the reduced set of eigenvectors corresponding to the identical eigenvalues.

Each matrix equation (14-k) has a sequence of N (eigenvalue;eigenvector) pairs, $\{(\lambda_n(k);V_n(k;\lambda_q(k))\}_n$, for a fixed reference gas k, and it is assumed here that the eigenvalues are arranged so that $$|\lambda_1(k)| \geq |\lambda_2(k)| \geq \ldots \geq |\lambda_N(k)| \quad (15\text{-}k)$$

and so that the highest magnitude eigenvalue in each set satisfies $$|\lambda_1(k1)| \geq |\lambda_1(k2)| \geq \ldots |\lambda_1(kN)|, \quad (16)$$

where $\{k1, k2, \ldots, kN\}$ includes each of the integers $\{1, 2, \ldots, N\}$ precisely once. The eigenvector $V(k1;\lambda_1(k1))$ is identified as a first basis vector $V'(1)$:

$$V'(k1;\lambda_1(k1)) = V(k1;\lambda_1(k1)) \quad (17\text{-}1)$$

A second modified vector $$V'(k2;\lambda_1(k2)) = V(k2;\lambda_1(k2)) - \{V(k2;\lambda_1(k2)), V'(k1;\lambda_1(k1))\} V'(k1;\lambda_1(k1)) \quad 17\text{-}2$$

is computed, where $\{V(k2;\lambda_2(k2)), V'(1)\}$ is the scalar product (also referred to as the inner product) of the vectors $V(k2;\lambda_2(k2))$ and $V'(k1)$. More generally, a pth modified vector $$V'(kp;\lambda_1(kp)) = \quad (17\text{-}p)$$
$$V(kp;\lambda_1(kp)) - \sum_{r=1}^{p-1} \{V(kp;\lambda_1(kp)), V'(kr;\lambda_1(kr))\} V'(kr;\lambda_1(kr))$$

is computed for $p = 2, \ldots, K$. The set of vectors $\{V'(kr;\lambda_1(kr))\}_k (r = 1, \ldots, K)$ is mutually orthogonal, in the sense that the scalar products satisfy $$\{V'(kr;\lambda_1(kr)), V'(ks;\lambda_1(ks))\} = \delta_{r,s}. \quad (18)$$
$$> 0 (r = s)$$
$$= 0 (r \neq s).$$

Each of the set of vectors $\{V'(kr;\lambda_1(kr))\}_r (r=1, \ldots, K)$ is maximally independent of each of the other vectors in the set, in the sense of mutual orthonormality (Eq. (18)). Each vector $V'(kr;\lambda_1(kr))$ will have relatively large (primary) contributions from some of the sensor sub-arrays and will have smaller (secondary) contributions from the remainder of the N sub-arrays. The vectors $V'(kr;\lambda_1(kr))$ identify a maximally independent set of linear combinations of EPV responses from the N sub-arrays that can be used to distinguish presence of one reference gas (target molecule kr) from presence of another reference gas (target molecule ks). For example, if the set of reference gases are $H_2O_2$, $H_2O$ and $CH_3OH$, $N=3$ and three matrix eigenvalue equations are to be solved in Eqs. (9-k) (k=1, 2, 3). More generally, presence or absence of any of K target molecules ($K \geq 2$) may be estimated.

The linear combinations LC(kp) of EPV measurements for the different sensor sub-arrays correspond to modified principal components for the particular reference gases chosen. Choice of another set of another set of reference gases will result in a different set of modified principal components, although change of one or more concentration values within a reference gas may have little or no effect on the modified principal components.

The preceding analysis concerning EPV measurements and estimates of concentration can be done wholly at the data processing site, partly at each of the data processing site and at the chemical sensor module site, or wholly at the chemical sensor module site. The system provides an integrated chemical sensor system based on use of SWCNTs as sensing elements, including some preliminary testing results. The associated data transmission system is wireless, small, portable, and readily deployable in the field.

A nanostructure, or assembly of such structures, can be grown, for example, by a procedure discussed in connection with FIG. 1 in "Controlled Patterning And Growth Of Single Wall And Multi-wall Carbon Nanotubes," issued to Delzeit and Meyyappan in U.S. Pat. No. 6,858,197, incorporated by reference herein.

What is claimed is:

1. A system for receiving, analyzing and communicating results of sensing chemical and/or physical parameter values, the system comprising:

N sensors numbered $n=1, \ldots, N$ ($N \geq 2$), of parameters, where each sensor senses an electrical parameter value $EPV(t_{m,n};n)$ of a selected chemical or a physical parameter at a selected sequence of times $\{t = t_{m,n}\}_m$ ($m=1, 2, \ldots$), where at least one sensor senses a data set that includes at least one of a local temperature, a local vapor pressure, a local relative humidity, at least one of an acoustic signal and an electromagnetic signal for estimating a distance between the sensor and a reference surface, and presence of a selected chemical in a test gas, and where each sensor comprises a nanostructure (NS), having a sensing element having a diameter no greater than about 20 nm;

wherein at least one NS is loaded with a selected sensitizing substance drawn from a group of sensitizing substances comprising Au particles, located between first and second ends of the at least one NS, and the first and second ends are connected to first and second terminals, respectively, of at least one of a voltage source and a current source, and to an electrical parameter value measurement mechanism that measures a change in at least one of electrical current, voltage difference, electrical resistance, electrical conductance and capacitance between the first and second ends of the at least one NS;

a multiplexer, having at least N input terminals and at least one output terminal, that receives at least one of a sensed value $EPV(t_{m,n};n)$ and a sensed value change $\Delta EPV (t_{m,n};n)$ from sensor no. n, at a sequence of times, $\{t = t'_{m,n}\}$, where the time $t'_{m,n}$ is determined with reference to a corresponding time $t_{m,n}$, and where each of a first sequence of times $\{t_{m,n1}\}_m$ is interleaved with a second sequence of times $\{t_{m,n2}\}_m$ for at least two integers, n1 and n2, satisfying $1 \leq n1 < n2 \leq N$;

a wireless transmission module, connected to the multiplexer output terminal, to receive and transmit at least one of the sensed value $EPV(t_{m,n};n)$ and the sensed value change $\Delta EPV(t_{m,n};n)$, received from the multiplexer, for at least one sensor no. n; and a computer that is programmed to receive, from the wireless transmission module, and to compare at least one of the second value $EPV(t_{m,n};n)$ and the measured sensed value change $\Delta EPV(t_{m,n})$ in an electrical parameter value with a corresponding reference value and to estimate and indicate, based upon the comparison, presence or absence of at least one chemical in a group of K target chemicals, numbered $k = 1, \ldots, K$ ($K \geq 1$), where the N sensors, the multiplexer and the wireless transmission module are contained in a volume having a diameter no greater than about 14 cm.

2. The system of claim 1, wherein said multiplexer is located adjacent to at least one of said sensors.

3. The system of claim 1, wherein:
at least one of said sensors is exposed to said test gas to be interrogated for presence or absence of one or more of said K target chemicals in said test gas (k=1, . . . ,K; K≧1);
measurement values EPV(n;test) are provided of a selected electrical parameter for said test gas for each said of sensor no. n=1, . . . , N (N≧2), for each of said K target chemicals and for each of a selected sequence of concentrations Ck (k=1, . . . , K; K≦N) of the target molecule no. k; and
wherein said computer is further programmed:
to provide at least N+1 functional relationships $$EPV(G_{ref}; meas; n) = a_{0,n} + \sum_{k=1}^{K} a_{k,n} Ck(ref),$$

$$EPV(G_{ref}; meas; n; C = 0) = a_{0,n},$$

relating a reference gas configuration, $G_{ref}=G(\{Ck(ref)\})$, in which target chemical no. k, is present in a reference gas with a known, non-negative concentration value Ck(ref) (k=1, . . . , K), to a test measurement value $EPV(G_{ref};meas;n)$ of the reference gas that is sensed by said sensor no. n, where $a_{0,n}$ and $a_{k,n}$, are known calibration coefficients that are independent of concentration values present, and $a_{0,n}$ is an EPV value that would be measured by said sensor no. n in a test gas when all of the concentration values Ck are 0;
to receive or provide a sequence of test measurement values, $V_n(G;meas)$ and $V_0(G;meas)$, on said test gas in a gas configuration $G=G(\{Ck\})$, where at least one of the concentration values Ck of a target chemical is unknown;
to provide a numerical-valued error function $\epsilon(\{Ck\})$ associated with the test measurement values $V_n(G;meas)$, where the error function is defined by $$2\epsilon(\{Ck\}) = \sum_{n=1}^{N} w_n \left| EPV(G; meas; n) - EPV(G; meas; 0) - \sum_{k=1}^{K} a_{n,k} Ck \right|^p$$

where $w_n$ are selected non-negative weight coefficients and p is a selected positive number;
to provide at least K equations relating the calibration coefficients $a_{0,k}$ and $a_{n,k}$ for k=1, . . . , K, by partially differentiating the error function $\epsilon(\{Ck\})$ with respect to each of the concentration values Ck, and setting each of the partially differentiated expressions of $\epsilon(\{Ck\})$ equal to 0; and
to obtain solutions Ck for the at least K equations, for k=1, . . . , K, and to interpret these solutions as optimal solutions for the concentration values Ck.

4. The method of claim 3, wherein said computer is further programmed to choose said positive number p to be p=2P, where P is a positive integer.

5. The system of claim 3, wherein said computer is further programmed:
to receive a test measurement value for each of said N sensors for a new test gas, where said concentration value of at least one of said K target molecules in the new test gas is not yet known;
to provide said error function $\epsilon(\{Ck\})$, where said calibration coefficients, $a_{0,k}$ and $a_{n,k}$, are determined as in claim 3 and said concentration values Ck (k=1, . . . , K) are treated as initially unknown;
to minimize said error function $\epsilon(\{Ck\})$ with respect to a choice of value of at least one selected concentration value C(k=k1) (1≦k1≦K); and
to interpret the at least one selected concentration value C(k=k1) as a most likely value of said concentration value for said target molecule no. k1 in said new test gas.

6. The system of claim 5, wherein said computer is further programmed:
to minimize said error function $\epsilon(\{Ck\})$ with respect to a choice of value of each of said selected concentration values Ck (1≦k≦K) for said new gas;
to compute a value of said error function $\epsilon(\{Ck\})=\epsilon(min)$ using said selected concentration values for said new gas; and
when the value $\epsilon(min)$ is no greater than a selected error function threshold, $\epsilon(thr)$, interpreting satisfaction of this condition as indicating that target gases are the primary components of said new gas.

7. The system of claim 1, wherein a frequency of transmission of a first reporting cycle for said first sequence changes monotonically relative to a frequency of transmission of a second reporting cycle for said second sequence in response to change of a length of said first reporting cycle relative to a length of said second reporting cycle.

8. The system of claim 7, wherein said computer is further programmed:
to minimize said error function $\epsilon(\{Ck\})$ with respect to a choice of value of each of said selected concentration values Ck (1≦k≦K) for said new gas;
to compute a value of said error function $\epsilon(\{Ck\})=\epsilon(min)$ using said selected concentration values for said new gas; and
when the value $\epsilon(min)$ is greater than a selected error function threshold, $\epsilon(thr)$, interpreting satisfaction of this condition as indicating that at least one gas that is not one of said target gases is also a primary component of said new gas.

9. The system of claim 1, wherein said frequency of transmission of said first reporting cycle decreases monotonically, relative to said frequency of transmission of said second reporting cycle, as said length of said first reporting cycle increases relative to said length of said second reporting cycle.

10. The system of claim 1, wherein said sensors, said multiplexer and said wireless transmission module together consume no more than about 60 mWatt electrical power in operation.

* * * * *